United States Patent

Poli et al.

[11] Patent Number: 6,147,213
[45] Date of Patent: Nov. 14, 2000

[54] DIASTEREOMERICALLY PURE 3-OXO AND 3-THIOXO-4-AZA-ANDROSTAN DERIVATIVES AND THE USE THEREOF AS ANTIANDROGENS

[75] Inventors: Stefano Poli; Roberto Girardello; Vincenzo Olgiati; Ambrogio Magni; Paride Grisenti, all of Quinto de'Stampi, Italy

[73] Assignee: Polichem S.A., Val Fleuri, Luxembourg

[21] Appl. No.: 08/879,442

[22] PCT Filed: Dec. 18, 1995

[86] PCT No.: PCT/EP95/05008

§ 371 Date: Aug. 4, 1997

§ 102(e) Date: Aug. 4, 1997

[87] PCT Pub. No.: WO96/20210

PCT Pub. Date: Jul. 4, 1996

[30] Foreign Application Priority Data

Dec. 23, 1994 [IT] Italy .................. MI94A2626

[51] Int. Cl.[7] .................................. C07D 221/18
[52] U.S. Cl. .................................................. 546/77
[58] Field of Search ................ 514/284; 546/77

[56] References Cited

FOREIGN PATENT DOCUMENTS

WO 94/03476  2/1994  WIPO .

OTHER PUBLICATIONS

Rasmusson et al., "Azasteroids: Structure–activity relationships for inhibition of 5.alpha.–reductase and or androgen receptor binding", J. Med. Chem., vol. 29, pp. 2296–2315, 1986.

*Primary Examiner*—Barbara Badio
*Attorney, Agent, or Firm*—Bucknam and Archer

[57] ABSTRACT

Disclosed are compounds of formula (A)

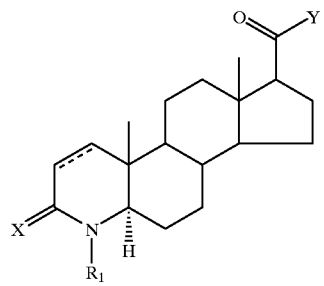

wherein X, $R_1$ and Y are as defined by the specification. The compounds are useful as antiandrogenic agents.

3 Claims, No Drawings

DIASTEREOMERICALLY PURE 3-OXO AND 3-THIOXO-4-AZA-ANDROSTAN DERIVATIVES AND THE USE THEREOF AS ANTIANDROGENS

This application is a 371 of PCT/EP95/05008 filed Dec. 18, 1995.

FIELD OF THE INVENTION

The present invention relates to azasteroid derivatives, in particular to diastereomerically pure 3-oxo- and 3-thioxo-4-aza-androstans derivatives having, at the 17β-position, a carboxylic group linked with an amido bond to a chiral primary amine with the asymmetric carbon at the α-position, the use thereof as antiandrogen agents and pharmaceutical compositions containing them.

BACKGROUND OF THE PRIOR ART

Testosterone, the main androgen present in bloodstream, acts directly on many target tissues, as such or as a reduced metabolite, i.e. dihydrotestosterone. The conversion into dihydrotestosterone is mediated by the enzyme 5-α-reductase, which is present in some target tissues. Dihydrotestosterone has a higher affinity to the androgen receptors than testosterone itself, moreover the hormone-receptor complex is more stable (Kaufman M., Pinsky L. *J. Steroid Biochem.* 1983, 18, 121–5; Wilbert D. M., Griffin J. E., Wilson J. D. *J. Clin. Endocrinol. Metab.* 1983, 56, 113–20). The inhibitors of the enzyme 5-α-reductase strongly bind to the enzyme, thus interfering in the transformation process of testosterone into dihydrotestosterone.

Up to now, a number of examples of inhibitors of the enzyme 5-α-reductase are known in literature; some having a steroidal structure (Rasmusson, G., H.; Reynolds, G. F.; Steimberg, N. G.; Walton, E.; Patel G. F.; Liang T.; Cacsieri M. A.; Cheung A. H.; Broocks J. R.; Berman C. Azasteroids: Structure-Activity Relationship for Inhibition of 5-α-Reductase and of Androgen Receptor Binding, *J. Med. Chem.* 1986, 29, 2298–2315. Holt D. A.; Levy M. A.; Oh H. J.; Erb J. M.; Heaslip J. I.; Brandt M.; Lan-Hargest H. Y.; Metcalf B. W. Inhibition of Steroid 5-α-Reductase by Unsaturated 3-Carboxysteroids, J. Med. Chem. 1990, 33, 943–950) other being nonsteroidal (EP 0 291 245 A2).

The pathologies connected with hyperandrogenicity conditions, in which these molecules might be used (benign prostatic hyperplasia, acne vulgaris, seborrhea, baldness, female hirsutism) are widespread. Though the therapy with this kind of medicaments proved to be effective, also as far as the life-quality offered to those suffering from said conditions is concerned, nevertheless it is not free from side-effects, therefore the development of novel, more potent inhibitors, which are more selective and better tolerated, is required (Charles D. J. et al. Nonsteroidal Inhibitors of Human Type 1 Steroid 5-α-Reductase, J. Med. Chem. 1993, 36, 421–423).

A 4-azasteroid conjugated at the 17β-position with a γ-amino acid (γ-aminobutyric acid) is known from EP 0 271 220. In the above cited Patent, a procedure for the preparation of a certain number of compounds oxidized at the carbamoyl branching at the 17-position is claimed.

SUMMARY OF THE INVENTION

Now it has surprisingly been found that, among all of the tested amino acid derivatives, those bearing an asymmetric carbon at the α-position to the amino acid carboxyl, have a marked inhibitory activity on the enzyme 5-α-reductase. In fact, for example, whereas the derivative bearing the amino acid glycine at the 17-position (compound Vd) proved to be a mild inhibitor of the above mentioned enzyme, all of the amino acids having an asymmetry centre at the α-position to the carboxylic group turned out to have a remarkable inhibiting action.

DISCLOSURE OF THE INVENTION

The present invention relates to diastereomerically pure compounds having the following general formula (A)

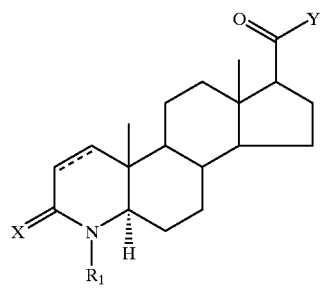

(A)

wherein:

the carbon-carbon bond at the 1–2 position can be single or double,

X can be an oxygen or sulfur atom;

$R_1$ can be a hydrogen atom or a straight or branched $C_1$–$C_4$ alkyl residue;

Y is the residue of an amino acid of formula

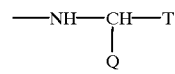

wherein T is the —COOH, or a —COOR$_3$ group, being $R_3$ a straight or branched $C_1$–$C_8$ alkyl residue; the group —CONHR$_4$ wherein R$_4$ is a straight or branched $C_1$–$C_8$ alkyl residue; or T is the group —CH$_2$OH;

Q represents the branching of a natural α amino acid of the (L) series or of the (D) series;

or Y is the group —NH—M, wherein M is a $C_4$–$C_{14}$ alkyl, cycloalkyl or $C_7$–$C_{14}$ arylalkyl group having an asymmetry centre at the α-position to the amine function;

the pharmaceutically acceptable salts thereof, the single diastereomeric and enantiomeric forms.

A first group of preferred compounds are the compounds of formula (A) wherein $R_1$ is selected from ethyl, methyl, hydrogen, Y is the group of formula

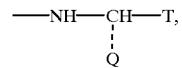

wherein Q and T are as defined above; or Y is the group —NH—M, wherein M is as defined above.

A second group of particularly preferred compounds are the compounds of formula (A) wherein $R_1$ is a hydrogen atom or a methyl group, Y is the group

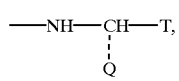

wherein Q and T are as defined above, or Y is the group —NH—M, wherein M is as defined above.

Particularly preferred are the compounds of formula (A) wherein:
- —X═O, $R_1$=H, Y is the residue of L-leucine ethyl ester and the carbon-carbon bond at the 1–2 position of the steroidal ring is single (compound Va);
- —X═O, $R_1$=H, Y is the residue of L-leucine ethyl ester and the carbon-carbon bond at the 1–2 position of the steroidal ring is double (compound VIa);
- —X═O, $R_1$=CH$_3$, Y is the residue of L-leucine N-methylamide and the carbon-carbon bond at the 1–2 position of the steroidal ring is single (compound Vb);
- —X═O, $R_1$=CH$_3$, Y is the residue of L-leucine ethyl ester and the carbon-carbon bond at the 1–2 position of the steroidal ring is single (compound Vc);
- —X═O, $R_1$=H, Y is the residue of L-phenylalanine methyl ester and the carbon-carbon bond at the 1–2 position of the steroidal ring is single (compound Ve);
- —X═O, $R_1$=H, Y is the residue of D-phenylalanine methyl ester and the carbon-carbon bond at the 1–2 position of the steroidal ring is single (compound Vf);
- —X═O, $R_1$=CH$_3$, Y=D(+)-α-methylbenzylamine and the carbon-carbon bond at the 1–2 position of the steroidal ring is single (compound Vg);
- —X═O, $R_1$=CH$_3$, Y=L(-)-α-methylbenzylamine and the carbon-carbon bond at the 1–2 position of the steroidal ring is single (compound Vh);
- —X═S; $R_1$=CH$_3$, Y is the residue of L-leucine N-methylamide and the carbon-carbon bond at the 1–2 position of the steroidal ring is single (compound Vi);
- —X═O, $R_1$=CH$_3$, Y is the residue of L-leucine wherein T is —CH$_2$OH and the carbon-carbon bond at the 1–2 position of the steroidal ring is single (compound IX).
- —X═O, $R_1$=CH$_3$, Y is the residue of (L)-leucine N-methylamide and the carbon-carbon bond at the 1–2 position of the steroidal ring is double (compound X);
- —X═O, $R_1$=CH$_3$, Y is the residue of (D)-leucine ethyl ester and the carbon-carbon bond at the 1–2 position of the steroidal ring is single (compound XI);
- —X═O, $R_1$=CH$_3$, Y is the residue of (D)-leucine N-methylamide and the carbon-carbon bond at the 1–2 position of the steroidal ring is single (compound XII);
- —X═O, $R_1$=CH$_3$, Y is the residue of (D)-phenylalanine methyl ester and the carbon-carbon bond at the 1–2 position of the steroidal ring is single (compound XIII).

Examples of straight or branched $C_1$-$C_8$ alkyl groups are methyl, ethyl, n-propyl, iso-propyl, n-butyl, sec-butyl, ter-butyl, n-pentyl, neo-pentyl, hexyl, octyl.

Examples of $C_4$-$C_{14}$ alkyl group, as defined by M, are: 2-butyl, 2-pentyl, 2-hexyl, 3-hexyl, 2-heptyl, 3-heptyl, 2-octyl, 3-octyl, 4-octyl, 2-decyl, 4-decyl.

Examples of $C_4$-$C_{14}$ cycloalkyl group, as defined by M, are: 1-methylcyclopropyl, 1-methylcyclobutyl, 1-methylcyclopentyl, 1-methylcyclohexyl.

Examples of $C_8$-$C_{14}$ arylalkyl groups, as defined by M, are: α-methylbenzyl, α-ethylbenzyl, α-propylbenzyl, α-methyl-1-naphthyl, α-methyl-2-naphthyl.

Examples of groups Q, which represent the branching of the natural α-amino acid

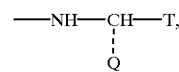

are the residues of Ala, Glu, Gly, Asn, His, Asp, Ile, Leu, Glu, Met, Phe, Trp, Val.

Examples of pharmaceutically acceptable salts are (for T═—COOH) those obtainable with inorganic or organic bases, such as triethanolamine, ethylenediamine, tetramethylammonium and tromethamine.

Another object of the present invention is a process for the preparation of compounds of formula (A).

A further object of the present invention is the use of the compounds of formula (A) for the preparation of a medicament having inhibitory activity on the enzyme testosterone 5-α-reductase.

Still another object of the present invention is a pharmaceutical composition containing at least one compound of formula (A) as the active ingredient.

DETAILED DISCLOSURE OF THE INVENTION

Contrary to EP 0 271 220, the present invention provides diastereomerically pure compounds, which can be prepared minimizing the risk of racemization of the carbon atom in a to the group 17β-CONH—.

According to the present invention, the compounds of general formula (A) can be prepared according to the following scheme 1.

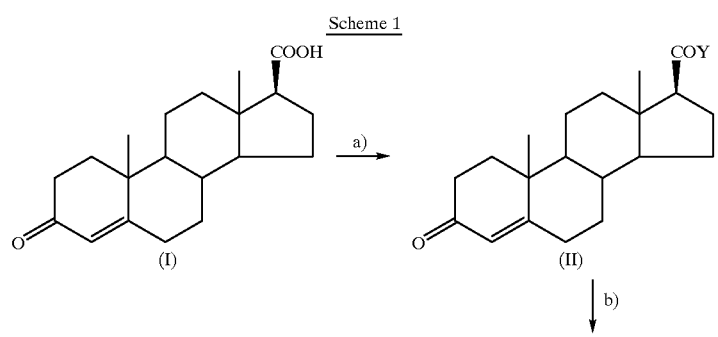

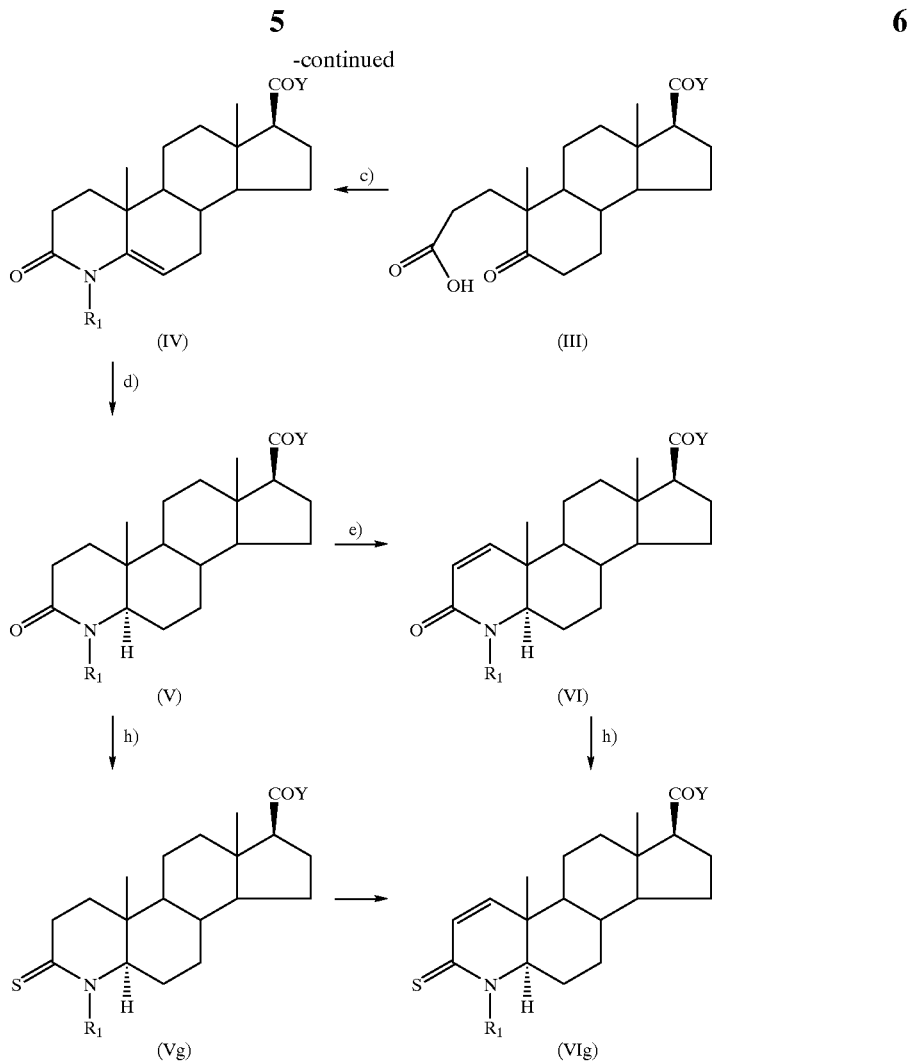

wherein the groups are as defined above.

The process comprises the following steps:

a) reaction of the compound of formula (I) with the compound HY, wherein Y is as defined above, to give the intermediate of formula (II);

b) transformation of the intermediate of formula (II) into the secosteroid of formula (III);

c) reaction of the secosteroid of formula (III) with an amine of formula NH₂R₁, wherein R₁ is as defined above, to give the 5–6 unsaturated azasteroid (IV);

d) reduction of the double bond at the 5–6 position of the azasteroid to give a compound of formula (A) wherein the carbon-carbon bond at the 1–2 position of the steroid is single; and, if desired;

e) unsaturation of the carbon-carbon bond at the 1–2 position of the steroid to give a compound of formula (A) wherein the carbon-carbon bond at the 1–2 position of the steroid is double; and, if desired;

f) transformation of a compound of formula (A), in which Y is —NH—CH(Q)—T, wherein T is —COOR₃, into a compound of formula (A) wherein T is —CH₂OH;

g) resolution of the enantiomeric mixture of compound of formula (A) obtained in the above steps; and, if desired;

h) thionation of the 3-position of the steroidal ring of the compound of formula (A) obtained in the above steps and optional unsaturation of the carbon-carbon bond at the 1–2 position of the steroid; and, if desired;

i) salification of the compound of formula (A) obtained in the above steps.

According to a general procedure, the compounds (A) wherein Y is —NH—CH(Q)—T and Q is the residue of the amino acid Ala, Glu, Gly, Asn, His, Asp, Ile, Leu, Gln, Met, Phe, Trp, Val were prepared starting from the known compound (I) according to scheme 2.

Scheme 2
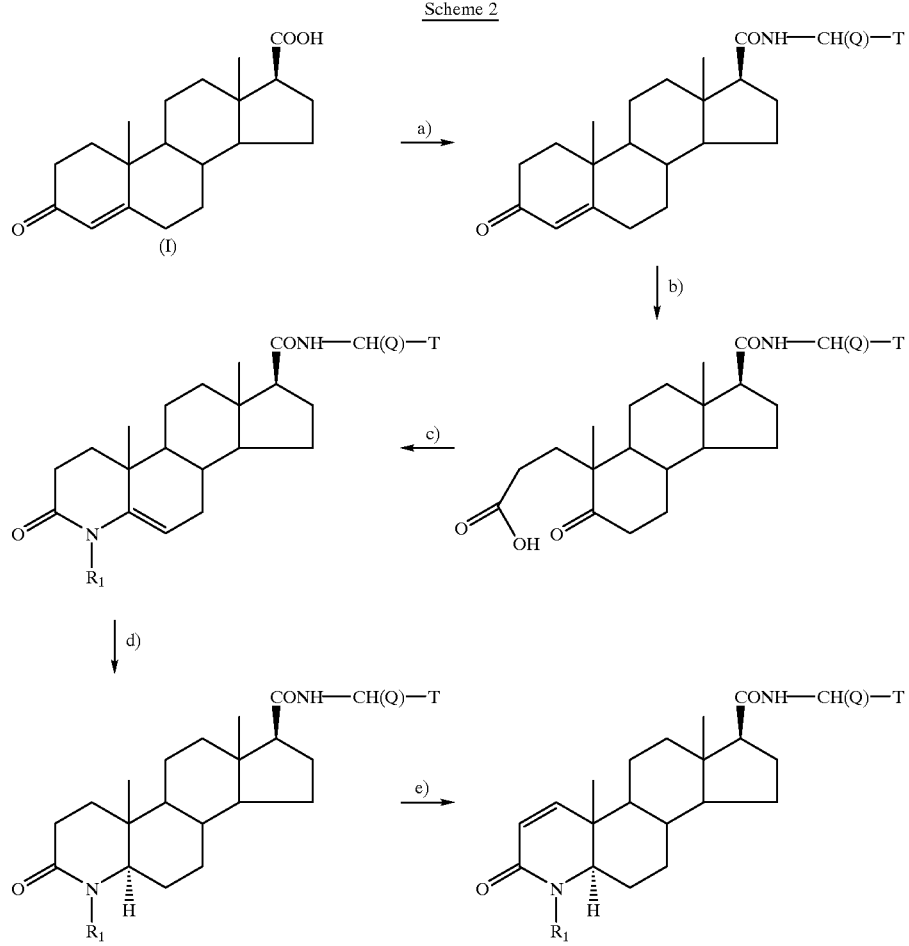
The process according to the invention comprises the following steps:
a) the compound of formula (I)
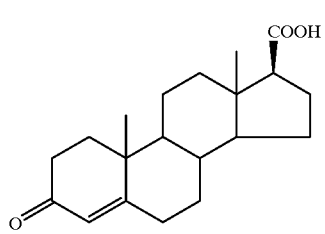
is reacted with a compound of formula H$_2$N—CH(Q)—T to give the amide of formula
b) said amide is transformed into the secosteroid of formula
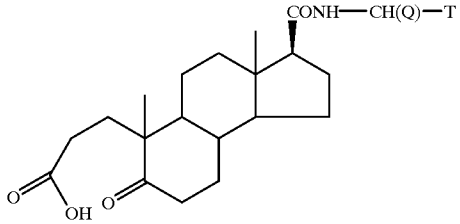
c) said secosteroid is reacted with an amine NH$_2$R$_1$, wherein R$_1$ is as defined above, to give the azasteroid of formula

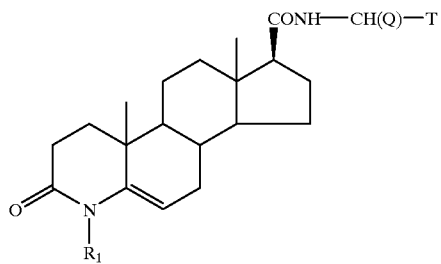

d) said azasteroid is hydrogenated to give a compound of formula (A) wherein the carbon-carbon bond at the 1–2 position of the steroidal ring is single; and, if desired;

e) said compound of formula (A) obtained in step d) is subjected to unsaturation of said 1–2 position;

f) resolution of the enantiomeric mixture of the compound of formula (A) obtained in the above steps; and, if desired;

g) transformation of the 3-oxo group into the 3-thioxo group of a compound of formula (A) obtained in the above steps; and, if desired;

h) salification of the compound of formula (A) obtained in the above steps.

The amino acid $NH_2$—CH(Q)—T, wherein Q and T are as defined above, used in the first reaction step a), is protected at the carboxylic function with conventional groups known in peptide synthesis, which groups cannot be removed by catalytic hydrogenation, for example an ester or amido group with an alcohol or a straight, branched, cyclic, polycyclic or heterocyclic alkyl amine. According to this procedure the compound (I) dissolved in an anhydrous aprotic solvent (such as tetrahydrofuran, hexane, preferably toluene) in concentrations ranging from 0.01 to 0.5 M and pyridine (about 1.3 moles per mole of substrate) is first reacted under inert atmosphere at a temperature range from −10 to +10° C. with oxalyl chloride (1.25 moles per mole of substrate) and left under vigorous stirring at this temperature for a time ranging between 30 minutes and 1 hour. After this time, a suspension of the amino acid protected at the carboxylic function and in the form of hydrochloride (in a ratio ranging from 3 to 5 moles per mole of substrate) in toluene and pyridine (the latter in an equimolar amount to the amino acid hydrochloride) is added in a time between 10 and 20 minutes. The reaction is then heated to a temperature ranging between 40 and 60° C. for a time from 0.5 to 6 hours. After this time the reaction is worked up as follows: pH is adjusted to 5 (1N HCl) and the mixture is extracted with dichloromethane. The organic phase is then dried over sodium sulfate and evaporated under vacuum recovering a crude which is subsequently purified by chromatography to give the desired amide in yields ranging from 60 to 80%. Subsequently (step b) the amide is dissolved in t-butanol (in concentrations ranging from 0.1 to 0.5 M) with a 19% sodium carbonate aqueous solution (780 ml per mole of substrate). The reaction temperature is then brought to a range between 70 and 80° C. and an aqueous solution (of the same volume as the t-butanol one) at he same temperature, of $KMnO_4$ (11.6 g per mole of substrate) and $NaIO_4$ (1.56 kg per mole of substrate) is slowly added with vigorous stirring so as to prevent an accumulation of an excess of oxidizing mixture (about 45 minutes). When the addition has been completed, the reaction is refluxed for a time ranging between 1 and 3 hours. The reaction is then worked up as follows: the mixture is cooled to room temperature keeping stirring for 30 minutes; then the formed solid is filtered off and the filtrate is concentrated under vacuum to about ⅓ of the starting volume. The resulting solution (kept at a temperature below 15° C.) is slowly acidified to pH 2 with conc. HCl under vigorous stirring. The resulting precipitate is recovered by filtration and dried under vacuum at a temperature of 80° C., thereby recovering the secosteroid in yields ranging from 70 to 85%. This compound is dispersed at a temperature of −10° C. in ethylene glycol at a concentration ranging from 0.2 to 0.4 M, then (step c) 10 to 30 moles of liquid ammonia or of the desired amine per mole of substrate are added. The reaction is then slowly heated (in a time between 30 and 60 minutes) at a temperature ranging between 140 and 180° C. for a time from 5 to 20 minutes. The reaction is then cooled at room temperature, diluted with water (volume to volume) and acidified to pH 2 with conc. HCl. The resulting precipitate is recovered by filtration under vacuum to give the desired azasteroid in yields ranging from 75 to 85%.

Alternatively, using the described procedure, the latter azasteroid (wherein T is —$CONHR_4$ and $R_4$ is $CH_3$, $CH_2CH_3$), can be obtained directly starting from the secosteroid (wherein T is $COOR_3$ and $R_3$ is alkyl) and increasing the amount of amine $R_4NH_2$ (from 20 to 80 moles per mole of secosteroi d) used during the closure reaction of the ring A and maintaining heating at 180° C. for a time ranging from 15 to 30 minutes. According to this alternative synthesis, $R_4$ will be the same as $R_1$ in the resulting azasteroid derivative; the yields of this step from the secosteroid intermediate to the desired azasteroid derivative range from 80 to 92%.

The azasteroid is hydrogenated (step d) in a methanol solution or in acetic acid in concentrations ranging from 0.05 to 0.2 M with 5% Pt/C or with 10% Pd/C (¹/₁₀ by weight compared with substrate) under a pressure ranging between 0.5 and 3 atm and at a temperature from 40 to 80° C. After a time varying between 30 minutes and 4 hours, the reaction is worked up by filtration over celite, evaporation of the solvent under vacuum and purification by crystallization from acetonitrile or chromatographic purification, to give the desired product, i.e. a compound of formula (A) wherein the carbon-carbon bond at the 1–2 position of the steroidal ring is single, in yields ranging between 50 and 90%. The Δ1 dehydrogenation (step e) is carried out according to conventional procedures of the steroid chemistry; thus the substrate is dissolved in concentrations ranging between 0.02 and 0.1 M in an aprotic solvent, such as toluene, diglyme or, preferably, chlorobenzene, with phenylselenic anhydride (1 to 1.5 equivalents per mole of substrate). The reaction is then heated at a temperature of 110° C. for a time between 3 and 18 hours, then the solvent is evaporated off under vacuum. The resulting crude is purified by silica gel chromatography (1/60 ratio, dichloromethane/acetone gradient solution) to give the desired product in yields ranging from 50 to 85%. Alternatively, the same compound can be obtained suspending the substrate in anhydrous dioxane, at a concentration ranging from 0.1 to 0.4 M, then adding in sequence DDQ (2,3-dichloro-5,6-dicyano-1,4-benzoquinone) (1 to 1.4 moles per mole of substrate) and N,O-bis(trimethylsilyl) trifluoroacetamide (BSTFA) (4 to 6 moles per mole of substrate). The reaction is stirred vigorously at room temperature for 4 hours and then at 110° C. for a time ranging between 8 and 24 hours. The reaction is worked up by diluting it 1:2 with dichloromethane and adding a 1% sodium bisulfite solution (1.41 ml per mmole of DDQ). The formed precipitate is filtered off and the organic phase is washed with 2N HCl, dried over sodium sulfate and evaporated to dryness. The resulting crude is then purified by crystallization from acetonitrile or methanol/water to give the desired product in yields ranging from 55 to 80%.

This process can be applied to the process of scheme 1, starting from compound (I) to yield compounds (V) and (VI), in which Y is —NH—CH(Q)—T, wherein T is not $CH_2OH$.

Alternatively, the amino acid can be conjugated to the azasteroid at the 17β-position according to scheme 3:

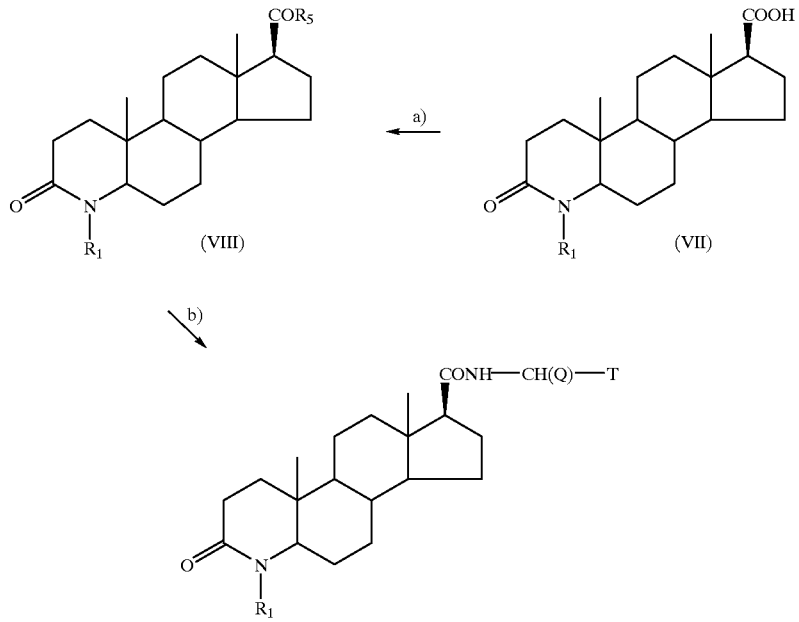

Scheme 3 wherein $R_1$, Q and T are as defined above and $R_5$ is a carboxy-activating group.

According to the invention, the process comprises the steps of:
a) activation of the carboxyl of the 17-β-carboxy-4-azasteroid of formula (VII);
b) reaction of the resulting intermediate with an amino acid of formula $H_2N$—CH(Q)—T, wherein Q and T are as defined above.

Following this synthetic scheme, starting from the known azasteroids (VII) (Rasmusson, G., H.; Reynolds, G. F.; Steimberg, N. G.; Walton, E.; Patel G. F.; Liang T.; Cacsieri M. A.; Cheung A. H.; Broocks J. R.; Berman C. J. Med. Chem. 1986, 29, 2298–2315), which have a carboxylic function at the 17β-position, the desired function can be introduced to attain the final compounds, first activating the acid (VII) with conventional activating groups, such as the pentafluorophenyl ester group or the 2-thiopyridyl derivative (Araki, M.; Sakata, S.; Takei, H.; Mukaiyama, T. *Bull. Chem. Soc. Jpn.* 1974, 47, 1777) to give the intermediates (VIII), which subsequently are reacted with the amino acid to be introduced. This procedure has been used successfully in particular for the preparation of the derivatives with Arg, Cys, Thr, Tyr, Ser, Lys, besides with the already considered amino acids. In this way, for example by reacting a suspension of the thiopyridyl ester (VIII) in a mixture of an apolar aprotic solvent, preferably tetrahydrofuran, in concentrations ranging from 0.04 to 0.2 M, with the desired amino acid (in a molar ratio ranging from 3 to 6 moles per mole of steroid), with vigorous stirring at a temperature ranging between 5 and 60° C. for a time from 8 to 48 hours, the desired products are obtained which can be purified from the reaction mixture by silica gel chromatography (gradient elution with dichloromethane/methanol) in yields ranging from 55 to 95%.

According to the present invention, the diastereomerically pure compounds of formula (A) can be obtained by different procedures for the resolution of the diastereomeric mixtures: for example, by a fractional crystallization procedure or by hydrolase-catalyzed resolution of the ester derivatives ($R_3$= straight alkyl groups up to 8 carbon atoms) (Santaniello E., Ferraboschi P., Grisenti P., Manzocchi A., Chem. Rev., 1992, 92, 1071–1140; Santaniello E., Ferraboschi P., Grisenti P.; Enzyme Microb. Technol., 1993, 15, 367–382) or finally by crystallization of the corresponding carboxylic derivatives with an enantiomerically pure amine. Such a procedure is applied to the different embodiments of preparation of the compounds of formula (A) according to the present invention.

Compounds of formula (A), wherein Y is the group —NH—M defined above, can be obtained through the synthetic schemes described above, using the chiral amine $H_2N$—M instead of the amino acid derivative.

As far as the preparation of the corresponding 3-thioxo derivatives (X=S) of the diastereomerically pure derivatives described above is concerned, these were prepared by a simple procedure using the Lawesson's reagent as the thionating agent (R. A. Cherkasov et al., Tetrahedron, 41(13), 1985, 2567–2624). Such a procedure has already been described in WO/9413691, published on Jun. 23, 1994, and it allows to obtain the corresponding compounds thionated at the 3-position with a high chemoselectivity degree with respect to the other present functions (for example amino and ester bonds). These products were prepared in yields ranging from 47 to 89%, according to scheme 4, in a single step starting from the corresponding 3-oxo derivatives (X=O) of general formula (A).

Scheme 4

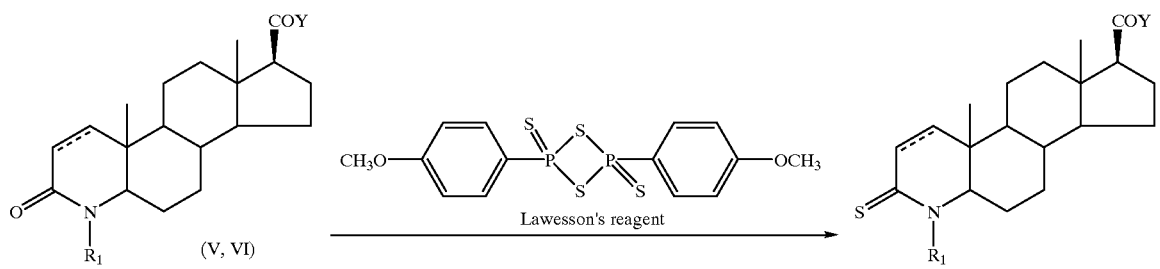

Starting from the amino acid derivatives obtained according to schemes 1, 2 or 3, the corresponding derivatives selectively reduced at the esterified carboxylic function of the amino acid could also be prepared. In this way, starting from the compounds of general formula (V) (T=—COOR$_3$), the corresponding alcoholic derivatives (IX) (T=—CH$_2$OH) could be prepared, according to the reaction scheme 5.

Scheme 5

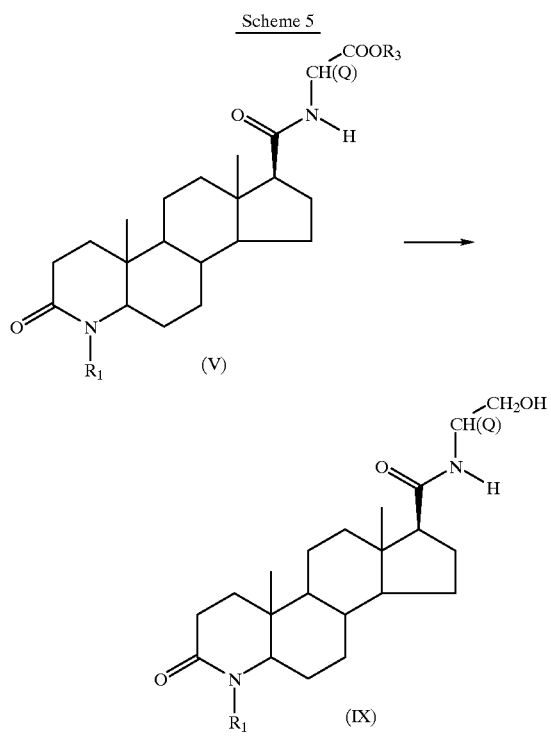

Following a general procedure, this reaction can be carried out in apolar aprotic solvents, such as tetrahydrofuran or diethyl ether, in concentrations ranging from 0.01 to 0.1 M, with stirring at room temperature, with a hydride such as lithium or calcium borohydride (1 to 1.4 mmoles per mole of substrate). The reaction is carried out with vigorous stirring at room temperature for a time ranging from 1 to 18 hours, and after decomposition of the hydride excess with acids, gives the desired product in yields ranging from 70 to 90%.

The compounds of formula (A) are active as inhibitors of testosterone 5-α-reductase and therefore are useful in human medicine, particularly in the treatment of the hyperandrogenetic conditions, such as acne vulgaris, seborrhea, female hirsutism, androgenetic alopecia. The compounds of the present invention are particularly useful in the treatment of prostatic hypertrophy and prostatic carcinoma. Therefore, a further object of the present invention is the use of the compounds of formula (A) for the preparation of a medicament having inhibitory activity on testosterone 5-α-reductase, in particular for the treatment of the hyperandrogenetic conditions as mentioned above, specifically in the treatment of prostatic hypertrophy and prostatic carcinoma.

The compounds of general formula (A) of the present invention are inhibitors of testosterone 5-α-reductase. The pharmacological efficacy of the compounds was evaluate by means of an in vitro test, intended to evaluated the direct interference on the tissue enzymatic activity, and a biological in vivo test.

In Vitro Test:

The activity of the compounds of formula (A) was tested on the enzyme testosterone 5-α-reductase in the rat prostate (Liang et al.; Endocrinology, 117, 571. 1985). An amount of fresh homogenate of rat prostate containing about 100 μg of proteins is incubated in 250 μl of Krebs/Ringer buffer in the presence of a system generating NADPH disodium salt (11.76×10$^{-2}$M) and glucose 6-phosphate-dehydrogenase (3.5×10$^{-2}$M U.I.) and of [$^{14}$C]-testosterone (3.16×10$^{-6}$M, specific activity about 56.9 mCi/mmole) as labelled substrate. Vials containing no proteins, are used to determine the blanks. The incubation is carried out in a stirring bath thermostatized at 37° C. for two hours with a 98:2 O$_2$/CO$_2$ flow. At the end of the incubation, the reaction is topped placing the samples into ice. In order to correctly qualify the two main 5-α-reduced metabolites which are formed in the prostate in these conditions (DHT and 3α-diol), prior to the extraction each sample is added with DHT and 3α-diol labelled with tritium (about 5,000 dpm) in order to evaluate the recovery. The formed metabolites are extracted twice with 5.5 ml of diethyl ether. The extracts, after dissolution in 200 μl of ethanol containing non-labelled DHT and 3α-diol as reference standard, are separated by thin layer chromatography using silica gel plates, eluted three times with a dichloromethane/diethyl ether 11:1 mixture at a temperature of 4° C. The spots of DHT and 3α-diol are developed with iodine vapours, whereas the testosterone ones by exposure to UV rays (UV adsorbtion of the 4–5 double bond, conjugated with the keto group at 3). The silica gel areas, in which DHT and 3α-diol group have been evidenced, are scraped and placed into count test-tubes. After the addition of 0.5 ml of water, in order to deactivate the steroidal bond to silica, and of 6 ml of scintillation liquid, the samples are placed onto a horizontal stirrer and stirred for 15 minutes. After decanting the suspended silica gel, the samples are counted in a liquid scintillation spectrometer. The values in dpm, obtained by a standard calibration curve, are corrected on the basis of the recovery percentage calculated on the tritiated steroids added to each sample prior to the extraction. The results are expressed in pg of steroid formed during the two hour incubation per mg of proteins. In each test, the $CI_{50}$ of the tested molecule was evaluated using different concentrations of the substance, from $10^{-5}$ to $10^{-9}$M.

The compounds of the present invention show a $CI_{50}$ ranging between 222 and 9 nM.

In Vivo Test:

The compounds of general formula (A), which are active in the in vitro inhibition of the enzyme testosterone 5-α-reductase, were studied in vivo to evaluate the inhibitory activity on the weight of the prostate and of the seminal vesicles in normal adults rats (Rittmaster R. S. et al. Molec. Endocrin., 5, 1023, 1991). Male rats CRL:CD(SD) BR, weighing 200–250 g, are treated orally for 4 consecutive days at a dose of 40 mg/kg/day according to the following scheme:

a control group receiving the solvent;

a group receiving finasteride as standard;

other groups treated with the tested substances.

24 Hours after the last treatment, rats are killed and prostate and seminal vesicles are withdrawn. The results are expressed as percent decrease in the weight of the two organs compared with the control group. The decrease in the prostate weight at the tested dose was 43–52%, and the decrease in the vesicles weight was 60–75%.

The present invention also relates to pharmaceutical compositions for the oral, parenteral and topical administrations containing at least one compound of formula (A) as the active ingredient in admixture with conventional carriers and excipients.

Examples of oral pharmaceutical compositions are tablets, capsules, sachets and suspensions; examples of parenteral compositions are freeze-dried ampoules or sterile suspensions; examples of topical compositions are creams, ointments, gel, aerosol or foams.

The compositions according to the invention are prepared with conventional methods, as for example those described in Remington's Pharmaceutical Sciences Handbook, Mack Pub., XVII Ed.; N.Y., U.S.A.

The daily dosage ranges from 5 to 50 mg; the unitary dose can contain 2.5 to 25 mg of active ingredient.

For the topical administration, the concentration of the active ingredient varies between 0.1 and 10% concentration, preferably 5%; the daily administrations can be one to two.

The following examples, with reference to the scheme reported above, further illustrate the invention.

EXAMPLE 1

2.14 g (6.77 mmoles) of compound (I) are dissolved in anhydrous toluene (34 ml) and pyridine (0.75 ml). The reaction is cooled to a temperature of 10° C. and, under vigorous stirring, a solution of oxalyl chloride (0.728 ml) in toluene (2 ml) is added. The reaction is maintained under stirring at a temperature of 10° C. for 1 hour. Then a suspension of L-leucine ethyl ester hydrochloride (6.6 g, 33.8 mmoles) in toluene (6 ml) and pyridine (2.71 ml) is added. The reaction is heated at a temperature of 40° C. for 4 hours, with vigorous stirring. After that ice (40 g) is added and the reaction pH is adjusted to 2 con 1N HCl, the organic phase is separated and the aqueous phase is extracted with dichloromethane (3×50 ml). The combined organic phases are then dried over sodium sulfate and evaporated under vacuum to give a crude, which is subsequently purified by silica gel chromatography (dichloromethane/methanol 9/1) 2.03 g (4.44 mmoles) of compound (II) are obtained, wherein Y=—CH(Q)—T is the residue of L-leucine ethyl ester, (66% yield).

$^1$H-NMR (60 MHz): 0.75 (s, 3H), 1.15 (s, 3H), 0.9–2.8 (complex system), 5.1 (s, 1H), 5.9 (s, 1H). Elementary analysis calculated for $C_{28}H_{43}O_4N_1$; Requires: C=73.49%, H=9.47%, N=3.06%; Found: C=73.51%, H=9.48%, N=3.08%.

The intermediate (II) (1.02 g, 2.23 mmoles) is dissolved in t-butanol (13 ml) and aqueous sodium carbonate (336 mg in 1.74 ml). The reaction temperature is then raised to 80° C. and an aqueous solution (13 ml) of $KMnO_4$ (26 mg) and $NaIO_4$ (3.48 g) at the same temperature is added with vigorous stirring in 45 minutes. When the addition is completed, the reaction mixture is refluxed for one hour. The reaction is then cooled to room temperature maintaining stirring for 30 minutes. The formed solid is filtered off and the filtrate concentrated under vacuum to about ⅓ of the starting volume. The resulting solution, after being cooled to 10° C., is slowly acidified to pH 2 with concentrated HCl under vigorous stirring. The formed precipitate is recovered by filtration and dried under vacuum at a temperature of 80° C. for 8 hours. The intermediate (III) is recovered, wherein Y=—CH(Q)—T is as defined above (810 mg, 1.7 mmoles) (76% yield).

$^1$H-NMR (60 MHz): 0.75 (s, 3H), 0.9–2.8 (complex system), 5.4 (m, exchangeable, 2H). Elementary analysis calculated for $C_{27}H_{43}O_6N_1$; Requires: C=67.90%, H=9.07%, N=2.93%; Found: C=67.91%, H=9.09%, N=2.96%.

1.07 g (2.24 mmoles) of compound (III) are dispersed at a temperature of −10° C. in ethylene glycol (6.5 ml), then liquid ammonia is added (1.02 ml). The reaction is slowly heated in 30 minutes to a temperature of 180° C. and subsequently kept at this temperature for minutes. The reaction mixture is then cooled at room temperature, diluted with water (volume to volume) and acidified to pH 2 with conc. HCl. The formed precipitate is recovered by filtration and dried at a temperature of 80° C. under vacuum to give 900 mg (1.96 mmoles) of compound (IV), wherein $R_1$ is hydrogen, Q and T are as defined above, (yield 88%).

$^1$H-NMR (60 MHz): 0.75 (s, 3H), 1.15 (s, 3H), 0.9–2.8 (complex system), 5.1 (s, 1H), 5.4 (s, 1H), 7.7 (m, 1H). Elementary analysis calculated for $C_{27}H_{42}O_4N_2$; Requires: C=70.71%, H=9.23%, N=6.11%; Found: C=70.73%, H=9.24%, N=6.15%.

586 mg (1.28 mmoles) of compound (IV) are dissolved in acetic acid (15 ml) with 500 mg of 5% Pt/C. The reaction is then hydrogenated at a pressure of 3 atm and at a temperature of 60° C. for two hours. After this time the reaction mixture is filtered over celite, the filtrate is evaporated to dryness, taken up into dichloromethane (20 ml) and washed until neutrality with a sodium bicarbonate aqueous solution. The organic phase is then dried over sodium sulfate, filtered and evaporated under vacuum to obtain a crude subsequently purified by crystallization from acetonitrile to give, in 86% yields, the desired product (Va) wherein the groups are as defined above and the carbon-carbon bond at the 1–2 position is single (506 mg, 1.1 mmoles).

MS m/e: 460 (M), 445 (M-15), 415 (M-45), 387 (M-73), 302 (M-158), 274 (M-186).

$^1$H-NMR (60 MHz): 0.65 (s, 3H), 0.85 (s, 3H), partially overlapped to 0.95 (d, 6H), 0.95–3.00 (complex system), 1.25 (t), 3.05 (m, 1H), 4.15 (q, 2H), 4.56 (m, 1H), 5.56 (d, 1H), 5.75 (m, 1H). Elementary analysis calculated for $C_{27}H_{44}O_4N_2$; Requires: C=70.40%, H=9.63%, N=6.08%; Found: C=70.42%, H=9.65%, N=6.09%.

EXAMPLE 2

The compound (Va) (760 mg, 1.65 mmoles) obtained in example 1 is dissolved in 6 ml of dioxane with DDQ (374 mg, 1.648 mmoles), and the resulting suspension, maintained under stirring at room temperature under $N_2$ atmosphere, is added with BSTFA (1.74 g, 6.969 mmol). The reaction is then kept under stirring at room temperature for 4 hours and then at 110° C. for 18 hours. The reaction is worked up pouring it into a stirred mixture of dichloromethane and 1% sodium bisulfite aqueous solution (2.34 ml). The heterogeneous mixture is then filtered to remove the formed precipitate and the organic phase is filtered, separated and washed with 2.9 ml of 2N HCl. Then the organic phase is dried over sodium sulfate, filtered and evaporated under vacuum to give a crude which is subsequently purified by chromatography (neutral alumine 1:100, grade 3°; elution in dichloromethane/methanol gradient). 450 mg (0.98 mmol, 60% yield) of the desired product (VIa) are recovered, wherein $R_1$ is H, Y=—NH—CH(Q)—T is the residue of (L)-leucine ethyl ester, the carbon-carbon bond at the 1–2 position is double.

MS m/e: 458 (M), 443 (M-15), 413 (M-45), 385 (M-73), 300 (M-158), 272 (M-186).

$^1$H-NMR (60 MHz): 0.60 (s, 3H), 1.00 (s, 3H), 0.90–2.65 (complex system), 1.25 (t), 3.2–3.4 (m, 1H), 4.15 (q, 2H), 4.56 (m, 1H), 5.7 (d, 1H), 6.8 (d, 1H). Elementary analysis calculated for $C_{27}H_{42}O_4N_2$; Requires: C=70.71%, H=9.23%, N=6.11%; Found: C=70.73%, H=9.25%, N=6.14%.

EXAMPLE 3

With a process similar to that described in example 2, compound (X) was prepared wherein X=O, $R_1$=$CH_3$, Y=—NH—CH(Q)—T is the residue of (L)-leucine N-methylamide and wherein the carbon-carbon bond at the 1–2 position of the steroidal ring is double.

MS m/e: 458 (M+), 428 (M-30), 400 (M-58), 315 (M-143), 287 (M-171); $^1$H-NMR (60 MHz): 0.65 (s, 3H), 0.90 (m, 9H), 0.70–2.30 (complex system), 2.8 (d, 3H), 3.00 (s, 3H), 3.30 (m, 1H), 4.40 (m, 1H), 5.70 (m, 2H), 6.60 (d, 1H). Elementary analysis calculated for $C_{27}H_{43}O_3N_3$; Requires: C=70.86%, H=9.47%, N=9.18%; Found: C=70.84%, H=9.42%, N=9.12%.

EXAMPLE 4

5 g (10.47 mmol) of the compound (III) of example 1 are dissolved in ethylene glycol under stirring at room temperature, then the solution is cooled at a temperature of −10° C. and methylamine (26 ml) is added. The solution is heated slowly until reaching a temperature of 180° C., this temperature being maintained for 20 minutes. The reaction is then cooled at room temperature and acidified with 3N HCl. The formed precipitate is recovered by filtration and dried under vacuum at a temperature of 80° C. The resulting crude intermediate (4.250 g, 9.3 mmol) is used without further purifications in the subsequent reaction. For analytical purposes, a crude sample was purified by silica gel chromatography (1:80; elution with dichloromethane/methanol 8/2).

MS m/e: 457 (M), 442 (M-15), 412 (M-45), 401 (M-56), 384 (M-73), 299 (M-158), 271 (M-186); Elementary analysis calculated for $C_{27}H_{43}O_3N_3$; Requires: C=70.86%, H=9.47%, N=9.18%; Found: C=70.85%, H=9.49%, N=9.15%.

1.4 g (3.06 mmol) of crude compound, obtained in the preceding step, is dissolved in glacial acetic acid (20 ml). The resulting solution is hydrogenated at a temperature of 75° C. and under a pressure of 3 atm over 5% Pt/C (1.4 g) for 6 hours. The catalyst is removed by filtration over celite and the filtrate is concentrated under vacuum. The resulting residue is dissolved in dichloromethane and washed to neutrality with a bicarbonate aqueous solution. The organic phase is then dried over sodium sulfate, filtered and evaporated to dryness to give a crude which is subsequently purified by silica gel chromatography (1/100; elution with dichloromethane/methanol 95/5). 1.2 g (2.61 mmol) of compound (Vb) are obtained, wherein $R_1$ is $CH_3$, Y=—NH—CH(Q)—T is the residue of (L)-leucine methylamide and the carbon-carbon bond at the 1–2 position of the steroidal ring is single (yield 85%).

MS m/e: 460 (M+1), 459 (M), 444 (M-15), 429 (M-30), 401 (M-58), 331 (M-128), 316 (M-146); $^1$H-NMR (60 MHz): 0.65 (s, 3H), 0.90 (m, 9H), 0.90–2.65 (complex system), 2.8 (d, 3H), 2.95 (s, 3H), 3.05 (m, 1H), 4.40 (m, 1H), 5.80 (d, 1H), 6.65 (m, 1H). Elementary analysis calculated for $C_{27}H_{45}O_3N_3$; Requires: C=70.55%, H=9.87%, N=9.14%; Found: C=70.56%, H=9.85%, N=9.11%.

EXAMPLE 5

With a process similar to that described in example 4, the compound (XII) was prepared, wherein X=O, $R_1$=$CH_3$, Y=—NH—CH(Q)—T is the residue of (D)-leucine N-methylamide and the carbon-carbon bond at the 1–2 position of the steroidal ring is single. Compared with compound (Vb), the compound (XII) shows a similar analytic profile as far as the $^1$H-NMR analysis (60 MHz) and mass fragmentation are concerned, whereas it is different at the $^1$H-NMR analysis (500 MHz): in fact, the signal of the C-18 methyl, which appears at 0.60 ppm in the compound Vb, is found at 0.66 ppm in the compound (XII).

Elementary analysis calculated for $C_{27}H_{45}O_3N_3$; Requires: C=70.55%, H=9.87%, N=9.14%; Found: C=70.51%, H=9.90%, N=9.10%.

EXAMPLE 6

2.420 g (12.38 mmol) of L-leucine ethyl ester hydrochloride are dispersed with vigorous stirring at room temperature in a mixture of anhydrous tetrahydrofuran (50 ml) and pyridine (1 ml). After 10 minutes, the thiopyridyl derivative (VIII) is added (wherein $R_5$ is thiopyridyl, $R_1$ is methyl) (939 mg, 2.204 mmol) and the resulting suspension is stirred at room temperature for 24 hours. The reaction mixture is concentrated to about ¼ of its starting volume and then purified by chromatography on basic alumine (elution with $CH_2Cl_2/CH_3OH$=98/2). 980 mg (2.068 mmol) of the desired product (Vc) are obtained, wherein X=O. $R_1$=$CH_3$, Y=—NH—CH(Q)—T is the residue of L-leucine ethyl ester and the carbon-carbon bond at the 1–2 position of the steroidal ring is single (94% yield).

MS m/e: 474 (M), 459 (M-15), 429 (M-45), 418 (M-56), 401 (M-73), 316 (M-158), 288 (M-186); $^1$H-NMR (60 MHz): 0.65 (s, 3H), 0.90 (m, 9H), 0.90–2.65 (complex system), 1.20 (overlapped to the above system), 2.9 (s, 3H), 2.9–3.1 (m, 1H), 4.15 (q, 2H), 4.56 (m, 1H), 5.56 (d, 1H). Elementary analysis calculated for $C_{28}H_{46}O_4N_2$; Requires: C=70.85%, H=9.77%, N=5.90%; Found: C=70.87%, H=9.75%, N=5.93%. $[\alpha]_D$=+21.0. $[\alpha]_{546}$=+26.0. $[\alpha]_{436}$=+49.9 (c=1CHCl$_3$).

EXAMPLE 7

With a process similar to that described above, the two diastereomers Ve (X=O, $R_1$=H, Y=L-phenylalanine methyl ester) and Vf (X=O, $R_1$=H, Y=D-phenylalanine methyl ester) were obtained, in both of which the carbon-carbon bond at the 1–2 position of the steroidal ring is single.

Analysis MS common to the two compounds Ve and Vf; MS m/e: 480 (M), 465 (M-15), 421 (M-59), 318 (M-162), 301 (M-179); Elementary analysis calculated for $C_{29}H_{40}O_4N_2$; Requires for Ve and Vf: C=72.47%, H=8.39%, N=5.83%; Found for Ve: C=72.50%, H=8.35%, N=5.81%; Found for Vf: C=72.51%, H=8.38%, N=5.85%. $^1$H-NMR (500 MHz, $CDCl_3$) for Ve: 0.62 (s, 3H), 0.86 (s, 3H), 3.0 (dd, 1H), 3.1 (m, 2H), 3.7 (s, 3H), 4.86 (m, 1H), 5.35 (m, 1H), 5.65 (m, 1H), 7.07 (m, 2H), 7.25 (m, 3H). $^1$H-NMR (500 MHz, $CDCl_3$) for Vf: 0.50 (s, 3H), 0.89 (s, 3H), 3.0 (m, 2H), 3.15 (m, 1H), 3.7 (s, 3H), 4.90 (m, 1H), 5.30 (m, 1H), 5.62 (m, 1H), 7.10 (m, 2H), 7.25 (m, 3H).

EXAMPLE 8

With a procedure similar to that described in example 6, compounds of formula (A) were prepared wherein X=O, $R_1$=$CH_3$, Y=D(+) and L(-) α-methylbenzylamine, respectively compound Vg and compound Vh.

$^1$H-NMR (60 MHz): of the D(+) α-methylbenzylamine derivative: 0.70 (s, 3H), 0.90 (s, 3H), 0.60–2.70 (complex system), 1.45 (d, overlapped to the preceding system), 3.00 (s, 3H), 2.90–3.15 (m, 1H overlapped to the preceding system), 5.2 (m, 1H), 6.80 (m, 1H), 7.45 (s, 5H).

$^1$H-NMR (60 MHz): of the L(-) α-methylbenzylamine derivative: 0.60 (s, 3H), 0.85 (s, 3H), 0.50–2.80 (complex system), 1.50 (d, overlapped to the preceding system), 3.00 (s, 3H), 2.90–3.15 (m, 1H overlapped to the preceding system), 5.2 (m, 1H), 6.80 (m, 1H), 7.45 (s, 5H). MS m/e: 437 (M), 422 (M-15), 332 (M-105), 317 (M-120), 289 (M-148); Elementary analysis calculated for $C_{28}H_{40}O_2N_2$; Requires: C=77.02%, H=9.23%, N=6.42%; Found for Vg: C=77.03%, H=9.26%, N=6.46%. Found for Vh: C=77.05%, H=9.25%, N=6.47%.

EXAMPLE 9

With a process similar to that described in example 6, the compound (XI) was prepared, wherein X=O, $R_1$=$CH_3$, Y=—NH—CH(Q)—T is the residue of (D)-leucine ethyl ester and the carbon-carbon bond at the 1–2 position of the steroidal ring is single. The compound shows the same characteristics at the MS and $^1$H-NMR (60 MHz) analysis as compound (Vc).

Elementary analysis calculated for $C_{28}H_{46}O_4N_2$; Requires: C=70.85%, H=9.77%, N=5.90%; Found: C=70.81%, H=9.74%, N=5.87%; $[α]_D$=+20.3, $[α]_{546}$=+24.1. $[α]_{436}$=+43.7 (c=1$CHCl_3$).

EXAMPLE 10

With a process similar to that described in example 6, the compound (XIII) was prepared, wherein X=O, $R_1$=$CH_3$, Y=—NH—CH(Q)—T is the residue of (D)-phenylalanine methyl ester.

$^1$H-NMR (500 MHz, $CDCl_3$): the diagnostic signals are reported: 0.47 (s, 3H), 0.85 (s, 3H), 2.40 (m, 2H), 2.89 (s, 3H), 2.96–3.18 (m, 3H), 3.70 (s, 3H), 4.90 (m, 1H), 5.60 (m, 1H), 7.10 (m, 2H), 7.25 (m, 3H). Elementary analysis calculated for $C_{30}H_{42}O_4N_2$; Requires: C=72.84%, H=8.56%, N=5.66%; Found: C=72.91%, H=8.58%, N=5.69%.

EXAMPLE 11

3.2 g (6.96 mmol) of compound (Vb), prepared according to example 4, are dissolved at room temperature in anhydrous dichloromethane (20 ml). This solution is added, under vigorous stirring, with 1.54 g (3.81 mmol) of Lawesson's reagent. The reaction is maintained under stirring at room temperature for 14 hours. The reaction mixture is then concentrated to about ½ of the starting volume and purified directly by silica gel chromatography (elution with $CH_2Cl_2$/$CH_3OH$ 95/5). 2.1 g of compound (Vi) are recovered, wherein X=S, $R_1$=$CH_3$, Y=—NH—CH(Q)—T is the residue of L-leucine methylamide and the carbon-carbon bond at the 1–2 position of the steroidal ring is single.

MS m/e: 475 (M), 446 (M-29), 332 (M-143), 304 (M-171); $^1$H-NMR (60 MHz): 0.60 (s, 3H), 0.90 (m, 9H), 0.90–2.65 (complex system), 2.75 (d, 3H), 2.85 (s, 3H), 2.8–3.0 (m overlapped to the preceding system, 2H), 3.1 (m, 1H), 4.60 (m, 1H), 6.20 (d, 1H), 7.20 (m, 1H). Elementary analysis calculated for $C_{27}H_{45}O_2N_3S_1$; Requires: C=68.17%, H=9.53%, N=8.83%, S=6.74; Found: C=68.20%, H=9.59%, N=8.80%, S=6.73.

EXAMPLE 12

420 mg (0.886 mmol) of compound (Vc), obtained in example 6, are dissolved in anhydrous tetrahydroauran (16 ml) with stirring at room temperature. After that, stirring at room temperature, $LiBH_4$ (23 mg, 1.056 mmol) is added. The reaction is stirred at room temperature for 12 hours and then neutralized with N HCl. The organic phase is evaporated under vacuum and the aqueous phase extracted with dichloromethane (3×9 ml). The organic extracts are then dried over sodium sulfate, filtered and evaporated to dryness to give a crude subsequently purified by silica gel chromatography (1/40; elution with dichloromethane/methanol 95/5). 341 mg (yield 89%) of compound (IX) are obtained, wherein X=O, $R_1$=$CH_3$, Y=—NH—CH(Q)—T is the residue of (L)-leucine, with T=$CH_2OH$ and the carbon-carbon bond at the 1–2 position of the steroidal ring is single.

MS m/e: 432 (M+), 417 (M-15), 414 (M-18), 402 (M-30), 316 (M-116); $^1$H-NMR (60 MHz): 0.65 (s, 3H), 0.85–0.91 (m, 9H), 0.70–2.40 (complex system), 2.85 (s, 3H), 2.90–3.10 (m, 1H), 3.5 (m, 3H), 4.0 (m, 1H), 5.55 (m, 1H). Elementary analysis calculated for $C_{26}H_{44}O_3N_2$; Requires: C=72.18%, H=10.25%, N=6.47%; Found: C=72.20%, H=10.22%, N=6.49%.

What is claimed is:

1. A compound of formula (A):

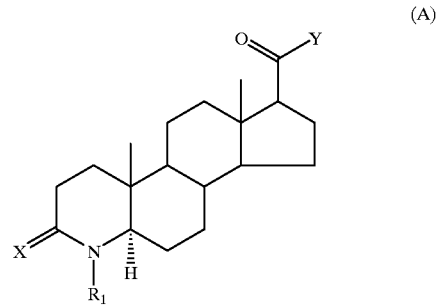

wherein:
the carbon-carbon bond at the 1–2 position is single:
X is an oxygen or a sulfur atom;
$R_1$ is a hydrogen atom or a straight or branched $C_1$–$C_4$ alkyl residue;

Y is the residue of an amino acid of formula

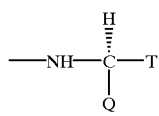

wherein T is the group $CH_2OH$;

Q represents the branching of α natural at amino acid of the (L) series or of the (D) series selected from the group consisting of glutamic acid, histidine, aspartic acid, leucine, phenylalanine, tryptophan, valine, asparagine and isoleucine.

2. A compound of formula (A)

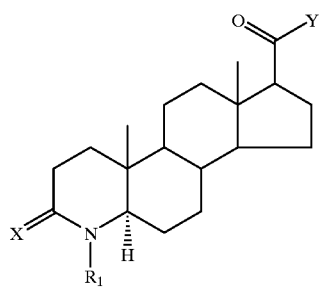

wherein:

the carbon-carbon bond at the 1–2 position is single;

X is an oxygen or a sulfur atom;

$R_1$ is a hydrogen atom or a straight or branched $C_1$–$C_4$ alkyl residue;

Y is the group —NH—M, wherein M is a member selected from the group consisting of α-methylbenzyl, α-ethylbenzyl, and α-propylbenzyl.

3. A compound of formula (A):

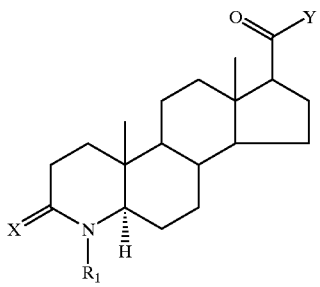

wherein:

—X=O, $R_1$=$CH_3$, Y=D(+)-α-methylbenzylamine, and the carbon atom at the α-position to the amine function is asymmetric.

* * * * *